(12) United States Patent
Niemiec et al.

(10) Patent No.: US 8,014,232 B2
(45) Date of Patent: *Sep. 6, 2011

(54) DRUG DELIVERY MANAGEMENT SYSTEM

(75) Inventors: Mark A. Niemiec, Ponte Vedra, FL (US); Louis M. Heidelberger, Villanova, PA (US)

(73) Assignee: Stanley Black & Decker Inc., New Britain, CT (US)

( * ) Notice: Subject to any disclaimer, the term of this patent is extended or adjusted under 35 U.S.C. 154(b) by 551 days.

This patent is subject to a terminal disclaimer.

(21) Appl. No.: 11/948,478

(22) Filed: Nov. 30, 2007

(65) Prior Publication Data

US 2008/0099366 A1    May 1, 2008

Related U.S. Application Data

(60) Continuation of application No. 11/931,863, filed on Oct. 31, 2007, now Pat. No. 7,612,662, which is a continuation of application No. 11/187,727, filed on Jul. 22, 2005, now Pat. No. 7,304,913, which is a division of application No. 10/234,022, filed on Sep. 3, 2002, now Pat. No. 6,961,285, which is a continuation-in-part of application No. 09/901,475, filed on Jul. 9, 2001, now Pat. No. 6,574,166, which is a continuation-in-part of application No. 09/611,582, filed on Jul. 7, 2000, now Pat. No. 6,411,567.

(51) Int. Cl.
G04B 47/00 (2006.01)
B65D 83/04 (2006.01)
G08B 13/14 (2006.01)

(52) U.S. Cl. ............ 368/10; 206/531; 340/539.12; 340/568.1

(58) Field of Classification Search .......... 368/10; 206/531–534.1; 221/2, 3, 15; 340/309.16, 340/531, 532, 539.12, 539.32, 572.1, 572.8, 340/686.1, 687, 568.1; 700/241, 244; 702/177
See application file for complete search history.

(56) References Cited

U.S. PATENT DOCUMENTS

| 4,258,354 | A |   | 3/1981 | Carmon et al. |
| 4,526,474 | A |   | 7/1985 | Simon |
| 4,617,557 | A | * | 10/1986 | Gordon ............ 340/309.7 |
| 4,660,991 | A | * | 4/1987 | Simon ................. 368/10 |

(Continued)

FOREIGN PATENT DOCUMENTS

DE    19522294 C2    6/1997

(Continued)

OTHER PUBLICATIONS

Allen, Daphne , "Using Bar Codes to Reduce Medical Errors", Pharmaceutical & Medical Packaging News: Bar Code Supplement, Mar. 2000, pp. 51-65.

(Continued)

*Primary Examiner* — Vit Miska
(74) *Attorney, Agent, or Firm* — Adan Ayala

(57) ABSTRACT

The present invention relates to assisting patients in the taking of medication, and to assisting third parties in accumulating information regarding patient medication intake. The invention may be embodied a system including a portable medication monitor used in association with an instrumented medication package to provide intake data acquisition and patient support functions. The system may further be connected to a computer or computer network allowing information distribution between the medication monitor and third parties, such as physicians or pharmacists.

10 Claims, 9 Drawing Sheets

U.S. PATENT DOCUMENTS

| | | | |
|---|---|---|---|
| 4,749,875 A | | 6/1988 | Hara |
| 4,971,221 A | | 11/1990 | Urquhart et al. |
| 5,313,439 A | | 5/1994 | Albeck |
| 5,412,372 A | | 5/1995 | Parkhurst et al. |
| 5,583,831 A | * | 12/1996 | Churchill et al. ............... 368/10 |
| 5,623,242 A | * | 4/1997 | Dawson et al. ................ 340/7.3 |
| 5,751,661 A | | 5/1998 | Walters |
| 5,774,865 A | * | 6/1998 | Glynn ................................ 705/2 |
| 5,827,180 A | | 10/1998 | Goodman |
| 5,852,590 A | | 12/1998 | de la Huerga |
| 5,902,234 A | * | 5/1999 | Webb ............................. 600/300 |
| 6,004,020 A | * | 12/1999 | Bartur ........................... 700/236 |
| 6,032,155 A | * | 2/2000 | de la Huerga .............. 707/104.1 |
| 6,150,942 A | * | 11/2000 | O'Brien ..................... 340/573.1 |
| 6,198,383 B1 | | 3/2001 | Sekura et al. |
| 6,294,999 B1 | * | 9/2001 | Yarin et al. ................. 340/573.1 |
| 6,332,100 B1 | * | 12/2001 | Sahai et al. .................... 700/242 |
| 6,366,206 B1 | | 4/2002 | Ishikawa et al. |
| 6,411,567 B1 | * | 6/2002 | Niemiec et al. ................ 368/10 |
| 6,529,446 B1 | | 3/2003 | de la Huerga |
| 6,574,166 B2 | * | 6/2003 | Niemiec ......................... 368/10 |
| 6,633,796 B1 | | 10/2003 | Pool et al. |
| 6,771,174 B2 | | 8/2004 | Broas |
| 6,839,304 B2 | * | 1/2005 | Niemiec et al. ................ 368/10 |
| 6,861,954 B2 | | 3/2005 | Levin |
| 2002/0026330 A1 | | 2/2002 | Klein |
| 2002/0104848 A1 | | 8/2002 | Burrows et al. |
| 2003/0007421 A1 | * | 1/2003 | Niemiec et al. ................ 368/10 |
| 2003/0016122 A1 | | 1/2003 | Petrick |
| 2003/0160698 A1 | | 8/2003 | Andreasson |
| 2004/0008123 A1 | | 1/2004 | Carrender |

FOREIGN PATENT DOCUMENTS

WO 98/36727 A1 8/1998

OTHER PUBLICATIONS

Bens Newsletter, (visited Apr. 17, 2000) http://www.packexpo.com/templates/BensNewsletter.cfm>.

Lubinsky, Annie, "Source Tagging Increases Sales", Pharmaceutical & Medical Packaging News, Feb. 2000, pp. 38-45.

Raeburn, Paul, "The Weak Link in the Drug-Safety Chain: Doctors", Business Week, 2000, p. 50.

"Finally, A Drug Package for the Forgetful", Packaging Strategies, 2000.

* cited by examiner

DRUG DELIVERY MANAGEMENT SYSTEM

CROSS-REFERENCE TO RELATED APPLICATIONS

This application is a continuation of U.S. patent application Ser. No. 11/931,863 Oct. 31, 2007 now U.S. Pat. No. 7,612,662, which is a continuation of U.S. patent application Ser. No. 11/187,727 Jul. 22, 2005 now U.S. Pat. No. 7,304,913, which is a divisional of application Ser. No. 10/234,022, now U.S. Pat. No. 6,961,285, filed Sep. 3, 2002, which is a continuation-in-part of application Ser. No. 09/901,478, now U.S. Pat. No. 6,574,166, filed Jul. 9, 2001, which is a continuation-in-part of application Ser. No. 09/611,582, now U.S. Pat. No. 6,411,567, filed Jul. 7, 2000. The entire disclosures of U.S. patent application Ser. No. 11/931,863, U.S. patent application Ser. No. 11/187,727 and U.S. Pat. No. 6,961,285 are incorporated by reference herein as if set forth in their entireties.

FIELD OF THE INVENTION

The present invention pertains to the accumulation and dissemination of information associated with the taking of medications, and more particularly to the acquisition, dissemination, and utilization of information obtained through implementation of an instrumented medication package.

BACKGROUND OF THE INVENTION

The explosive developments in medical treatment relating to drugs have created a costly and high risk drug management environment. A 1995 study published in the "Archives of Internal Medicine" estimates that $76 billion is spent each year in the U.S. on extra doctor visits and hospitalization because people do not take their medication properly. In addition, a 1999 study by the National Academy of Science, Institute of Medicine, describes errors made in the hospitals which threaten patients health. The study estimated that 98,000 patients die each year because of medical mistakes. Prescription drug errors are one of the major areas where mistakes are made.

Unit-dose blister type packaging for prescription drugs is one of the fastest growing package formats and is projected to be at 40% penetration in the U.S. market by 2003. Blister packages are already the dominant prescription drug package format in Europe with 85% penetration. Some of the reasons behind this growing use of blister packaging are: (i) product integrity being maintained throughout out the drug life cycle, (ii) better product protection to insure quality and efficacy of the drug, (iii) better tamper evidencing and child resistance, and (iv) improved patient compliance in that unit-dose blister packaging gives patents a clearly marked individual dosage.

The ability to obtain data regarding the usage of medications through a blister pack containing devices for monitoring the accessing of individual containments within the packaging is described in several references, including Applicant's U.S. patent application Ser. No. 09/611,582. These references teach monitoring the accessing of individual containments to determine whether and when a medication was taken, in order to accumulate information regarding the medication intake.

The taking of medications has become a central aspect of life. Individuals may take over the counter or prescription medications for a wide range of ailments. The effectiveness of the medications may be dependant on a patient's punctuality of application or ingestion (hereinafter referred to generically as "medication intake") of the medication at issue.

The punctuality with which a patient takes medication may affect every entity in the health care chain. The patient taking the medication on time increases the likelihood that the medication will be effective, thus reducing disadvantages associated with the medical condition for which the medication is being taken. These disadvantages may include work time lost due to the condition as well as patient discomfort associated with the condition. The improved effectiveness associated with timely medication also benefits physicians, by reducing the likelihood that the medication will be unsuccessful in resolving the condition, thus reducing the likelihood that additional visits are required to resolve the condition. Increased effectiveness associated with timely medication may also reduce the total amount of medication needed to be taken by a patient, thus reducing the cost of resolving the medical condition, such that expenses to health care insurers are reduced.

In order to assess the compliance of a patient taking medication according to an intake schedule, instrumented medication packages have been developed. These packages incorporate a method of identifying the dispensation of medication from the package. The inclusion of a clock allows the information to be correlated to time. Early efforts used some form of memory associated with the package to store dispensation time information for later downloading, such as when the package was returned to a pharmacy or other download-capable site. The necessity of returning the package to a specific location had several drawbacks, including the lack of incentive for a patient to return the package unless another prescription was to be picked up. Additionally, the dispensation information would not be available to anyone in the chain of entities involved in the treatment of the patient (the chain may include, but is not limited to, a doctor, pharmacist, insurer, medication manufacturer, the patient him or herself, other caregivers, or anyone else involved in the treatment of the patient) until after the package had been returned, and any data downloaded.

Applicant's earlier patent application disclosed the use of a network of receivers for receiving information from instrumented medication packages. One embodiment included the use of receivers located in hospital rooms to allow in-hospital monitoring of medication intake. Another embodiment utilized receivers located at diverse locations, including pharmacies and patient residences, to provide broader coverage for acquiring information from instrumented medication packages. Additional embodiments included capabilities for monitoring additional conditions associated with the taking of medication, including the conditions of storage of the instrumented medication package itself.

SUMMARY OF THE INVENTION

The present invention is a system and process for assisting patients with medication compliance. The system combines an instrumented medication package with a portable medication monitor to provide support to the patient in taking medication as directed. The system and process may additionally be communicably connected to a third party computer or computer network to allow third parties to access information on the medication monitor or to provide information to the patient via the medication monitor. Additionally, the medication monitor, when connected to a third party computer or computer network may be used to collect data regarding medication compliance for use in determining the efficacy of medications being taken by the patient.

In one form, the present invention may be embodied in a medication monitoring system which includes an instrumented medication package. The instrumented medication may have a plurality of medication containments, each medication containments having an closure incorporating a severable connector. The instrumented medication package may also include an instrumented medication package receiver and an instrumented medication package transmitter. The instrumented medication package receiver may be used for receiving trigger signals, and the instrumented medication package transmitter may be used for transmitting information identifying the condition of the severable connectors. The system may also include a medication monitor. The medication monitor may have a medication monitor transmitter and a medication monitor receiver. The medication monitor transmitter may be used for transmitting a trigger signal, while the medication monitor receiver may be used for receiving information transmitted by an instrumented medication package transmitter.

In another form, the present invention may be embodied in an instrumented medication package having a plurality of medication containments. The medication containments each may have a closure having a severable connector. The instrumented medication package may further have an instrumented medication package transponder. The instrumented medication package transponder may be used for receiving trigger signals, and transmitting a response signal in response to the trigger signals. The instrumented medication transponder may further include passive radio frequency identification circuitry. The passive radio frequency identification circuitry may comprise circuitry which modifies a response signal generated by the passive radio frequency identification circuitry, said response signal utilizing the energy of the trigger signal.

In a still further form the present invention may be embodied in a portable medication monitor having a general purpose computing circuitry, and an instrumented medication package transceiver. The instrumented medication package transceiver may include a transmitter and a receiver for transmitting to and receiving signals from an instrumented medication package. The portable medication monitor may further have a network connection for communicably connecting the portable medication monitor to at least one remote computer. The portable medication monitor may also include software for monitoring instrumented medication packages which may be associated with the portable medication monitor.

In a still further form, the present invention may be embodied in a method for monitoring medication intake. The method may include providing an instrumented medication package and a medication monitor. A trigger signal may be emitted from the medication monitor and received by the instrumented medication package. When the trigger signal is received, the instrumented medication package may transmit information identifying the condition of severable connectors. The transmitted information may be received at the portable medication monitor, which may then forward the information to a remote computer via a network connection.

DETAILED DESCRIPTION OF THE INVENTION

Figure 1:
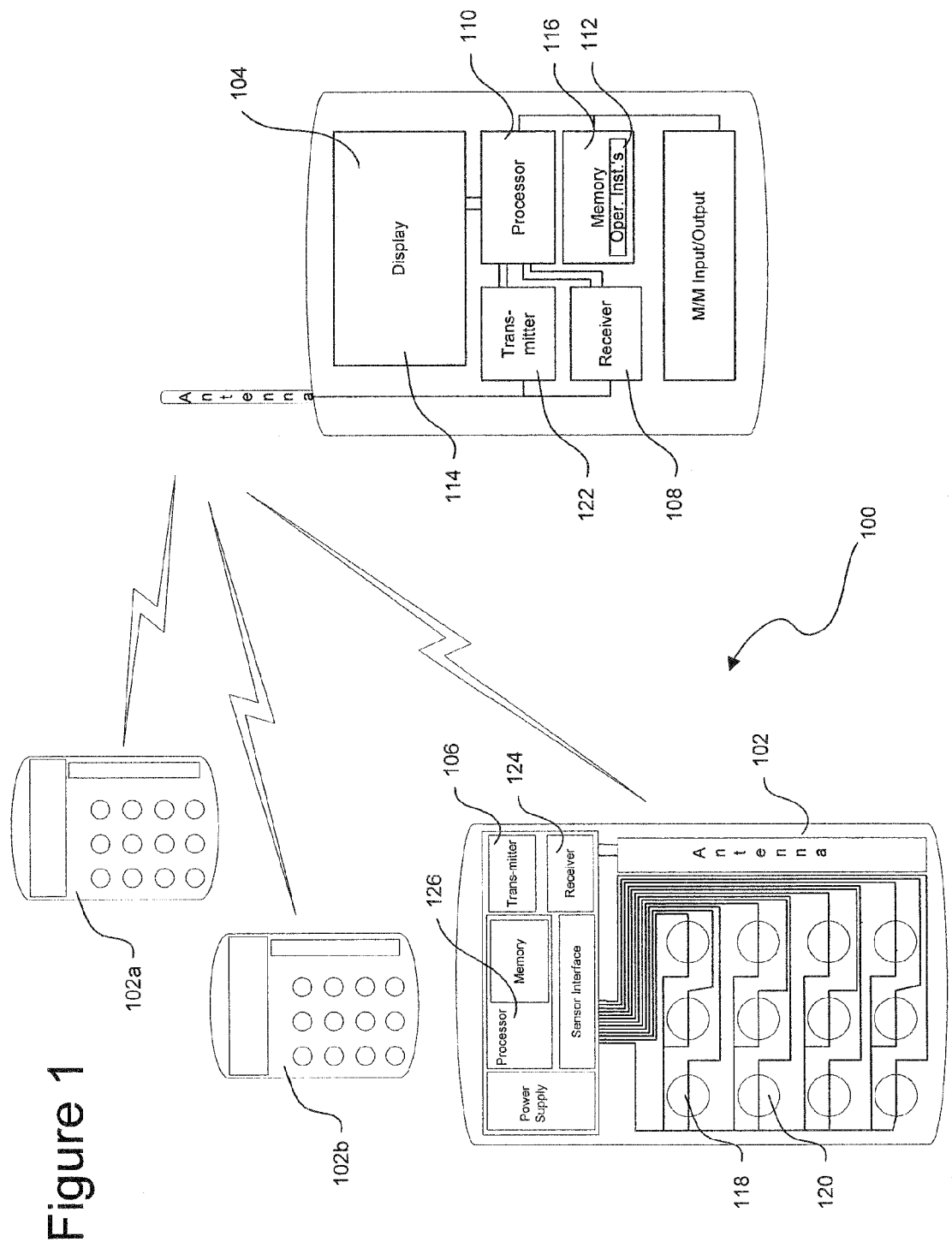
FIG. 1 illustrates an instrumented medication package associated with a medication monitor.

In FIG. 1, wherein like numbers represent like elements, there is shown an illustration of the components of a medication monitoring system 100 according to the present invention. The system may have an instrumented medication package 102 and a medication monitor 104 associated therewith. The instrumented medication package 102 includes a transmitter 106 capable of transferring information associated with the instrumented medication package 102 to the medication monitor 104. The medication monitor 104 includes a receiver 108 for receiving information from the instrumented medication package 102.

The medication monitor 104 is preferably portable, such that the medication monitor 104 may accompany a patient (not shown) as the patient travels. The medication monitor 104 may include a processor 110 which provides functionality for the medication monitor 104, such as in conjunction with operating instructions 112 or a computer program for communicating with the instrumented medication package 102 and handling data received from the instrumented medication package 102. The medication monitor 104 may also be provided with a display 114 such that a patient may receive information or reminders regarding medication to be taken. The display 114 may be aural tactile, or visual, or a combination thereof, such that reminders can be provided to a patient, such as a reminder that a dose of medication is due to be taken. The medication monitor may also include memory 116 to allow the medication monitor 104 to be used as a data accumulator, such that information retrieved from an instrumented medication package 102 may be removed from the instrumented medication package 102 once provided to the medication monitor 104, allowing reduced requirements for data storage integral to the instrumented medication package 102.

The medication monitor 104 may also be provided with functionality allowing information associated with the instrumented medication package 102 to be displayed for the patient taking the medication. The use of severable conductors 118 in association with medication containments 120 allows the detection of when a patient accesses medication (not shown). For example, a patient unsure of whether they took required medication on time would be able to review the times at which medication containments 120 were accessed, and compare this information with an intake schedule identifying when a dose was supposed to have been taken. Furthermore, the medication monitor 104 may be provided with functionality to allow a dosing schedule to entered into and displayed on the medication monitor 104, such that the patient would be easily able to determine when a dose should have been taken, as well as whether a dose was accessed at the requisite time.

The medication monitor 104 may also be provided with a transmitter 122 to allow the use of a transmission to trigger to be received by a instrumented medication package receiver 124 an information transfer from the instrumented medication package 102. The instrumented medication package 102 may utilize radio frequency identification technology to provide data transmission from the instrumented medication 102 package to the medication monitor 104. Radio frequency identification (RFID) technologies function as transponders, such that receipt of a trigger signal causes the RFID to respond with an identification transmission. The identification transmission may include data to be transmitted from the instrumented medication package 102 to the medication monitor 104, such as times at which severable conductors 118 were severed, or other information stored by the instrumented medication package 108.

Several methods for generating and types of trigger signals may be implemented. The use of radio frequency signals allows a triggering signal unique to the instrumented medication package 102 to be utilized. The use of the unique trigger signal reduces the likelihood that third parties would be able to generate a trigger signal to receive information from a instrumented medication package. The unique trigger signal may be associated with the actual medication package 102 itself, such that entry of an identifier into the medication monitor 104 may allow the medication monitor 104 to be able to generate a trigger signal for the instrumented medical package 102 for which an identifier has been provided.

The medication monitor 104 may also be provided with functionality to allow the medication monitor 104 to receive information from more than one instrumented medication package (102b, 102c) concurrently. As more than one medication may be required to be taken by a patient during a time period, the ability of the medication monitor 104 to acquire data and track multiple medications provides both an efficiency with regards to the acquisition of information, as well as a convenience to the patient, i.e., that a single medication monitor 104 may be used to support the taking of multiple medications.

In order to allow a single medication monitor 104 to receive information from more than one instrumented medication package (102, 102b, 102c), a method of deconflicting triggering and reception of information from the instrumented medication packaging may be implemented. Where active RFID's are used, one solution may be to impose a communications protocol allowing information to be transmitted both from the instrumented medication package 102 to the medication monitor 104, and from the medication monitor 104 to the instrumented medication package 102. The use of two way communications also allows additional communications security to be enable between the medication monitor 104 and an instrumented medication package 102, such that privacy issues regarding the medication and its usage may be maintained. The imposition of a protocol for such transmissions may also allow a single medication monitor 104 to be used with instrumented medication packages from various suppliers, such that a patient would not be required to maintain multiple medication monitors to allow the concurrent taking of multiple medications when those medications are from more than one supplier.

Active RFIDs typically use a triggered response form of two way communication to allow the conservation of power within the RFID. By only transmitting information in response to a trigger signal, power can be conserved by avoiding unnecessary transmissions. The use of trigger common to multiple devices, however, may allow an instrumented medication package 102 to transmit a response whenever a trigger signal is received, whether or not the trigger signal was intended for the instrumented medication package 102. Random triggering may also raise battery life concerns, especially if unintended triggers are frequently received. Common trigger signals also make it more likely that third parties can successfully trigger information transmissions from an instrumented medication package 102. Where health care is involved, privacy issues raise concerns regarding the ability of third parties to access patient care information. In the case of a medicated instrumentation package 102, information transmitted by a transmitter associated with the package may provide information to third parties. By limiting the validity of a trigger signal to a specific signal, such as the address identifying a specific instrumented medication package 102, the ability of third parties to trigger the transmission of information from an instrumented medication package 102 may be sufficiently curtailable to avoid privacy issues. The specific signal used may be implemented by providing to the medication monitor 104 an identifying number for the instrumented medication package 102, such as an identifier containing both random and non-random portions. For example, a portion of an identifier may serve to identify the manufacturer of the medication, while another portion contains a random number associated with the particular instrumented medication package 102. By implementing a manufacturer identifier, individual manufacturers may be able to implement the random number portion of the identifier without fear of duplicating an identifier from a different manufacturer, such as would be possible, albeit unlikely, if only a random number were used.

The processor 126 of the instrumented medication package 102 may monitor transmissions received by the instrumented medication package receiver 104 in order to detect receipt of a correct trigger. Receipt of a signal by the receiver 124 may trigger the instrumented medication package processor 126 to attempt to decode the signal to determine whether the signal contains the correct information. If the signal contains the correct trigger information, the processor 126 may trigger a transmission of information from the instrumented medication package 102, such as a list of medication cell accesses since a last transmission, or over a given period of time.

The incorporation of a unique identity associated with the trigger signal may also be used as part of an encryption algorithm, such that data transmitted from an instrumented medication package 102 may utilize the random portion of the package identifier as a seed for an encryption routine. Thus, the random number would need to be known in order to trigger a transmission, as well as to understand the meaning of the resultant transmission.

In one form, the medication monitor 102 may be implemented by the provision of specific functionality to a personal digital assistant (PDA). PDA's typically include the ability to accept add on modules, with control of the module being provided by the control circuitry of the PDA. In such an embodiment, the general functionality of the PDA may be utilized to provide the display and interface capabilities. Display functions could be accomplished through any display capable of generating a signal which can be sensed by a patient, such as a visual display, an auditory display (buzzer or other tone), or a vibratory display. Taste and smell displays are also feasible, although present technology limits the cost efficiency with which such displays can be generated.

The PDA may be provided with a transmitter/receiver modem capable of generating a trigger signal and receiving a responding transmission from an instrumented medication package. Although a radio frequency (RF) signal is discussed in the present implementation, light transmission, such as an infrared signal commonly used with items such as television remotes and calculators, may also be used, however such a signal may be limited in effectiveness due to its line of sight nature. An RF communications path using a frequency in common with pagers or cell phones could be susceptible to interference from cell phones and pagers being operated near the medication monitor 104 and instrumented medication package 102, especially if low transmission strengths are utilized to conserve power, or limit the ranges at which the signals could be received.

Accordingly, use of a frequency range dedicated to medication monitors may improve the performance of the monitors by avoiding interference from other transmitters. Multiple sets of medication monitors 104 and instrumented medication packages 102 operating in the same area may be problematic, in that transmissions associated with the individual medication monitors 104 and instrumented medication packages 102 could interfere with each other. In the absence of some other method of deconflicting signals, limiting the transmission power of the individual medication monitors 104 and instrumented medication packages 102 limits the range at which individual components would interfere with each other. Although not a perfect solution, utilization of power limited transmissions allows a single frequency to be used for instrumented medication packages 102, such that the cost of the transmitters 106 on the instrumented medication package 102, which may be disposable, may be kept at a minimum. Use of a common frequency furthermore increases the commonality of the medication monitor 104, such that the cost impediment to procuring a medication monitor 104 may be minimized.

Alternately, other methods of deconflicting the transmissions may be implemented. Where instrumented medication packages 102 can have the capability of transmitting at different frequencies, frequencies may be selected based on criteria likely to avoid generating conflicting transmissions. For example, a frequency could be selected based on the date of birth and first initial of a patient. The limitation to such an algorithm is the range of frequencies that an instrumented medication package 102 must be capable of transmitting over. The frequency range is a function of the frequency difference between two signal frequencies that is required to avoid intolerable interference between transmissions at the signal frequencies. Thus, the range may be determined by the number of signal frequencies to be implemented multiplied by the frequency difference. A tendency exists that the broader the range required of a transmitter 106, the higher the cost of the transmitter. Thus, minimizing the required range may allow reduced costs for the transmitter 106 associated with an instrumented medication package 102.

Although the description to this point suggests the association of a single patient with a medication monitor 104, a single medication monitor 104 may be utilized to monitor multiple patients concurrently. The ability to concurrently monitor multiple patients could be implemented simply by association of a patient identification with an instrumented medication package 102, 102b, 102c, when the instrumented medication package 102 was identified to the medication monitor 104. For instance, one person could monitor both his or her own medication concurrently with monitoring an instrumented medication package 102 containing medicine prescribed for a significant other, parent, or child. Alternately, multiple patient monitoring could be implemented to allow a nurse on a ward to ensure that medications for multiple patients were accessed correctly. These implementations are discussed further below.

Figure 2:
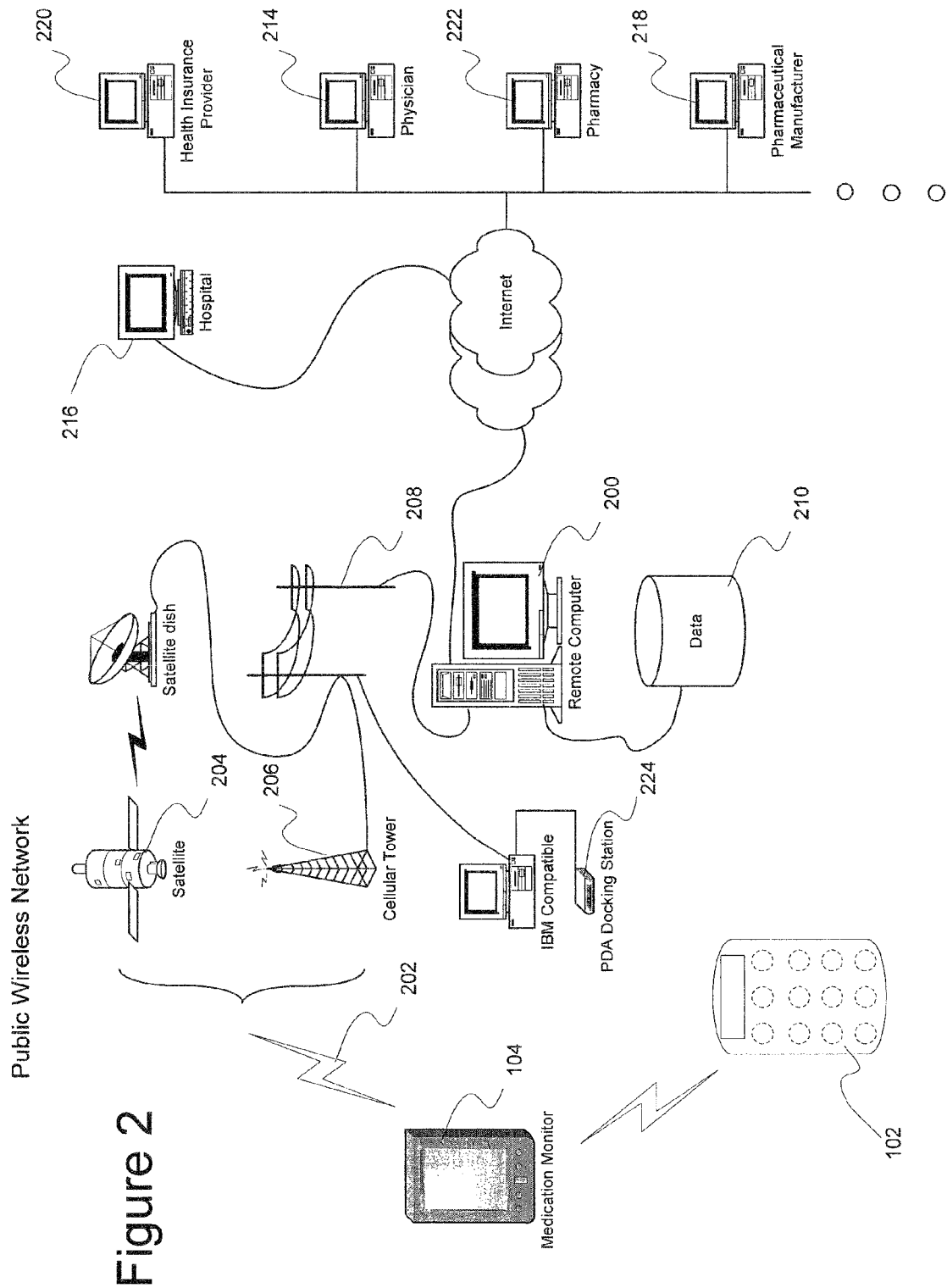
FIG. 2 illustrates an instrumented medication package associated with a medication monitor implemented within a health care network according to the present invention.

As generally illustrated in FIG. 2, the medication monitor 104 may be further provided with a remote communications capability, such as a capability to communicate with a remote computer 200 via a communications path 202. The communications path may be a wireless path, such as a satellite communications path 204 or a cellular transmission network 206 used with cell phones and/or other wireless handheld devices. Alternately, the communications path may be a publicly switched telephone network 208 (hereafter referred to as a "PSTN") path, or a pre-wired communications path, such as a connection to the internet, or other form of network connection. Such access may be gained by connecting the medication monitor 104 to a docking station 222.

The remote computer 200 may be a single computer or one of several computers in a network. The remote computer 200 may be communicably connected to the medication monitor 104 when a communications path 200 is established through one or more other computers, servers, or router. The remote computer 200 may contain a database 210 storing information associated with the medication taken by one or more patients. The remote computer 200 may also include a network access 212, such that third parties may access the stored data via a network. Additionally, the remote computer may be provided with e-mail or fax transmission capability, such that automated notices may be forwarded to recipients as indicated.

The third party access to the network may include access to the system by a physician through a physician's terminal 214, such that a physician could monitor the punctuality of a patient in accessing medication, or in determining what medication has been prescribed to a patient, such as what may occur when multiple physicians are responsible for the care of a single patient. Information concerning medications prescribed to a patient could include medications prescribed, as well as medication actually associated with a medication monitor 104, such that a physician could determine not only what medication was prescribed, but the status of a patient in completing a course of medication. This information could allow a physician to tailor a prescription to work best in a situation where drug interactions could adversely affect the efficacy of a particular medication.

A hospital terminal 216 could also be provided, to allow a hospital to determine present medication in the event that a patient was brought to an emergency room. Again, access to information identifying medications taken, and when last taken, would allow the hospital to more effectively treat the patient.

A pharmaceutical manufacturer access 218 could be provided to allow the pharmaceutical manufacturer to accumulate ongoing efficacy information regarding its products, such as information concerning the timeliness with which patients actually take medication, as well as whether courses of medication were completed, or not completed.

A health insurer access 220 could also be provided to allow an insurance carrier to better track medications dispensed to a patient. The health insurer access, in conjunction with a pharmacy access 222, could be implemented to allow prescriptions provided to the system through a physician access to be dispensed via the pharmacy access 222, and accounted for by the pharmacy access and health insurer accesses automatically, reducing the administrative overhead associated with the dispensation process. Further, where two way communications between the medication monitor 104 and the remote computer 200 have been implemented, identification information associated with a particular instrumented medication package 102 may be transferred directly from a pharmacy access 222 to a medication monitor 104 via the remote computer 200, removing the necessity of a patient entering data into the medication monitor 104 to associate a specific instrumented medication package 102 with the monitor 104.

Figure 3:
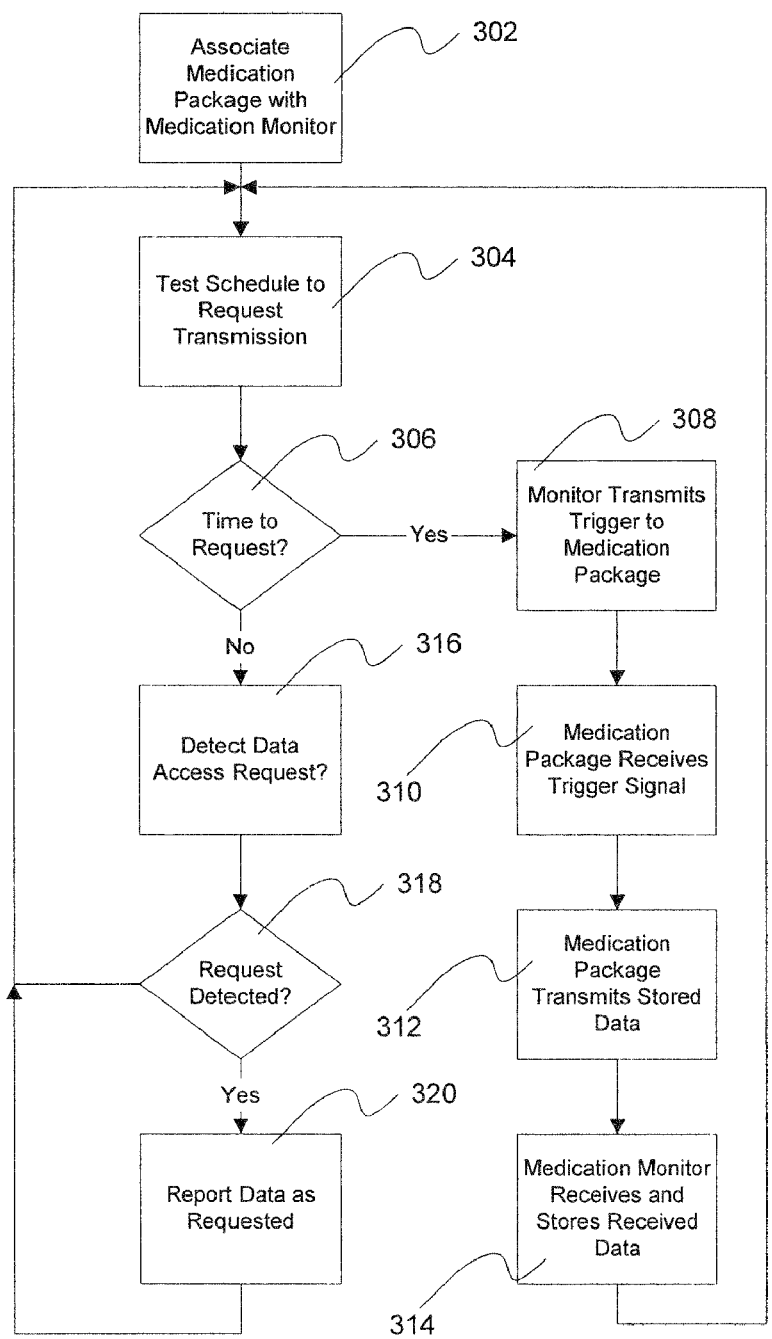
FIG. 3 shows a process flowchart illustrating a process of using a medication monitor in association with an instrumented medication package according to the present invention.

FIG. 3 illustrates a simple process embodying the present invention. An instrumented medication package 102 may be associated with the medication monitor 104. Association 302 informs the medication monitor 104 of the need to start monitoring information from the instrumented medication package 102. The association 302 step may include the provision of relevant information to the medication monitor 104, such as any identifiers for the instrumented medication package 102 needed to trigger a data transmission from the instrumented medication package. Additional information which may be associated is discussed further below.

Once the medication monitor 104 has been associated 302 with the instrumented medication package 102, the medication monitor 104 may begin monitoring the instrumented medication package 102 for transmitted information. The instrumented medication package 102 may be provided with instructions to periodically transmit data, such as in accordance with a predetermined schedule, or in response to the acquisition of data. Alternately, the instrumented medication package 102 may be provided with instructions to transmit acquired data in response to receipt of a valid trigger signal.

The use of a trigger signal as a means for instigating a data transmission from an instrumented medication package 102 may have several advantages. Where the instrumented medication package 102 transmits only in response to a trigger signal, power may be saved in the instrumented medication package 102 by the avoidance of transmissions when a medication monitor 104 is out of range of the instrumented medication package 102 transmitter 106. In order to verify range, the instrumented medication package 102 may be provided with discriminating circuitry to test the strength of a received signal. Signals below a threshold would be considered "out-of-range", such that the instrumented medication package 102 would not transmit data in response to receipt of an otherwise valid trigger. A range test could be important, especially where a medication monitor 104 incorporated a transmitter 122 having greater capabilities than the transmitter 106 of the instrumented medication package 102, causing an ability for the instrumented medication package 102 to receive signals transmitted by the medication monitor 104, while at the same time the medication monitor 104 would be unable to receive signals transmitted from the instrumented medication package 102. Such a signal strength test could be implemented as part of a trigger validation routine, such as where a unique identifier for the instrumented medication package 102 is implemented as a trigger validation method.

The schedule at which the medication monitor 104 triggers a transmission may be based on various patterns. In a simple schedule, the medication monitor 104 could attempt to trigger a transmission at a fixed frequency, such as once an hour. More complex schedules may be based on the dosing schedule of the particular medication, on a schedule based on the last successful triggering of a transmission, or based on a schedule provided by a patient.

For example, a patient could be prescribed a medication to be taken three times a day, two doses at each time. The patient could decide to take the medication at 6:00 AM, 3:00 PM, and 10:00 PM, in order to squeeze the three dosages into waking hours. The patient could provide the schedule to the medication monitor 104, which could then schedule attempts to trigger a transmission ½ hour after each scheduled time. Should a trigger attempt fail, the medication monitor 104 could be programmed to either reattempt to trigger a transmission at a certain amount of time after the failed trigger attempt, or could be programmed to generate an alarm requiring the patient to manually verify that a scheduled dosage had been taken. Alternately, if the medication monitor 104 was able to successfully trigger a transmission, and the transmission did not indicate that medication had been accessed, the medication monitor 104 could generate an alarm to warn a patient that a scheduled dosage had been missed.

Monitoring of an instrumented medication package 102, as illustrated, could be implemented by providing a schedule to a medication monitor 104. The provided schedule could be based on information provided with a basic monitoring program used by the medication monitor. Alternately, the schedule could be provided via a remote computer 200, or entered directly into the medication monitor 104 when an instrumented medication package 102 is associated with the medication monitor 104. The medication monitor 104 would then test 304 the schedule to determine whether it was the correct time to request a transmission from the instrumented medication package 102. Such a determination would be dependant upon the test schedule provided. For example, if the schedule instructed that a transmission be generated every hour, the medication monitor 104 could check a time counter to determine whether an hour had elapsed since the last trigger transmission. Alternately, where the schedule were based on generating a trigger transmission at a specific time, the medication monitor could compare the scheduled time with the time shown by an internal clock, and determine to generate a trigger transmission when the scheduled time and clock time were the same.

If it were determined 306 that the schedule indicated that a trigger transmission should be transmitted, the medication monitor could transmit 308 a trigger transmission. The instrumented medication package 102 would receive 310 the trigger transmission, and respond by transmitting 312 information to the medication monitor 104. The information could be as simple as an acknowledgment of receipt of the trigger signal, signifying an absence of relevant data to be reported, or a report merely informing the medication monitor which medication containment cells had been accessed. The transmission could also inform the medication monitor of other information, such as times when containment cells were accessed, or other parameters monitored by the instrumented medication package.

The transmitted information would be received 314 by the medication monitor, which could store the information, or disseminate the information to a remote computer 200, as indicated by the internal operating instructions 112 of the medication monitor 104. The medication monitor 104 could then return to waiting for the next scheduled trigger transmission time.

Concurrently with monitoring an associated instrumented medication package, the medication monitor 104 could monitor for data access requests forwarded by the remote computer. If a data access request were received 316, the medication monitor 104 could report 320 the requested data to the remote computer, and continue monitoring the instrumented medication package according to the schedule.

ALTERNATE EMBODIMENTS

The systems and method described above include functionality providing benefits beyond the illustrated association between a patient and a medication monitor 104. As noted, a medication monitor may be tasked with monitoring medication for more than one patient. A medication monitor 104 may also be associated with multiple patients, such as a medication monitor 104 being associated with a family having multiple members, such that one member could track medication usage of multiple members of the family, such as a mother tracking a teen-aged child's taking of an antibiotic for an ear infection, while simultaneously tracking her husbands taking of a medication for heartburn.

Alternately, the medication monitor 104 could be associated with a single medical care provider, such as a nurse, who is responsible for medication regimens for a group of patients. Implementation of communications path 202 between the remote computer 200 and the medication monitor 104 would allow the remote computer 200 to monitor medications accessed by the nurse for dispensation to patients, such that the medications accessed by the nurse could be monitored in a sufficiently rapid fashion to allow errors in accessing medication to be caught before the medication was delivered to patients. Such a communications path could be a direct connection between the medication monitor 104 and the remote computer 200, such as a wireless network connection. Furthermore, medications to be dispensed could be tracked via the remote computer 200, such that information identifying which medications to access for which patient could be downloaded from the remote computer 200 to the medication monitor 104. If single dosage blister packs were utilized for medication dispensation, a further check could be incorporated through the association of a patient with a specific room having a specific fixed receiver in addition to the nurse's medication monitor 104, such that accessing medication in a room for which the associated patient is not indicated would result in the triggering of an alarm through the medication monitor 104, indicating that the nurse should verify the medication being dispensed in the room.

Passive RFID Capabilities

In addition to relying on an active circuitry using an onboard power supply, the present invention may use a hybrid system combining active and passive circuitry to assist in the medication monitoring and dispensation. A passive system uses the energy of radio frequency transmissions as a power source for responding to a remote transmitter. The large advantage of a passive system is that no on-board power supply is required. The limitation is that the absence of an on-board power supply may limit the operation of monitoring circuitry when the RF transmission is not sufficiently strong to power the circuitry. Such a limit may also prevent the operation of a clock on the instrumented medication package 102.

Passive RF circuitry is used in anti-theft RFID systems, such that when the RFID tag is located within range of a RF transmitter transmitting on the required frequency, the passive RFID tag responds by transmitting an identification signal. Typically, the limitation of RF signal strength as a power source for the passive RFID limits a response to occurring when the RFID tag is 3-5 feet from the RF transmitter. The circuitry within the RFID may be hardwired such that software is not required in order for the RFID chip to function. The RFID chip thus may function as a circuit, rather than a general purpose computer executing instructions.

Hybrid Passive and Active Circuitry

Figure 4:
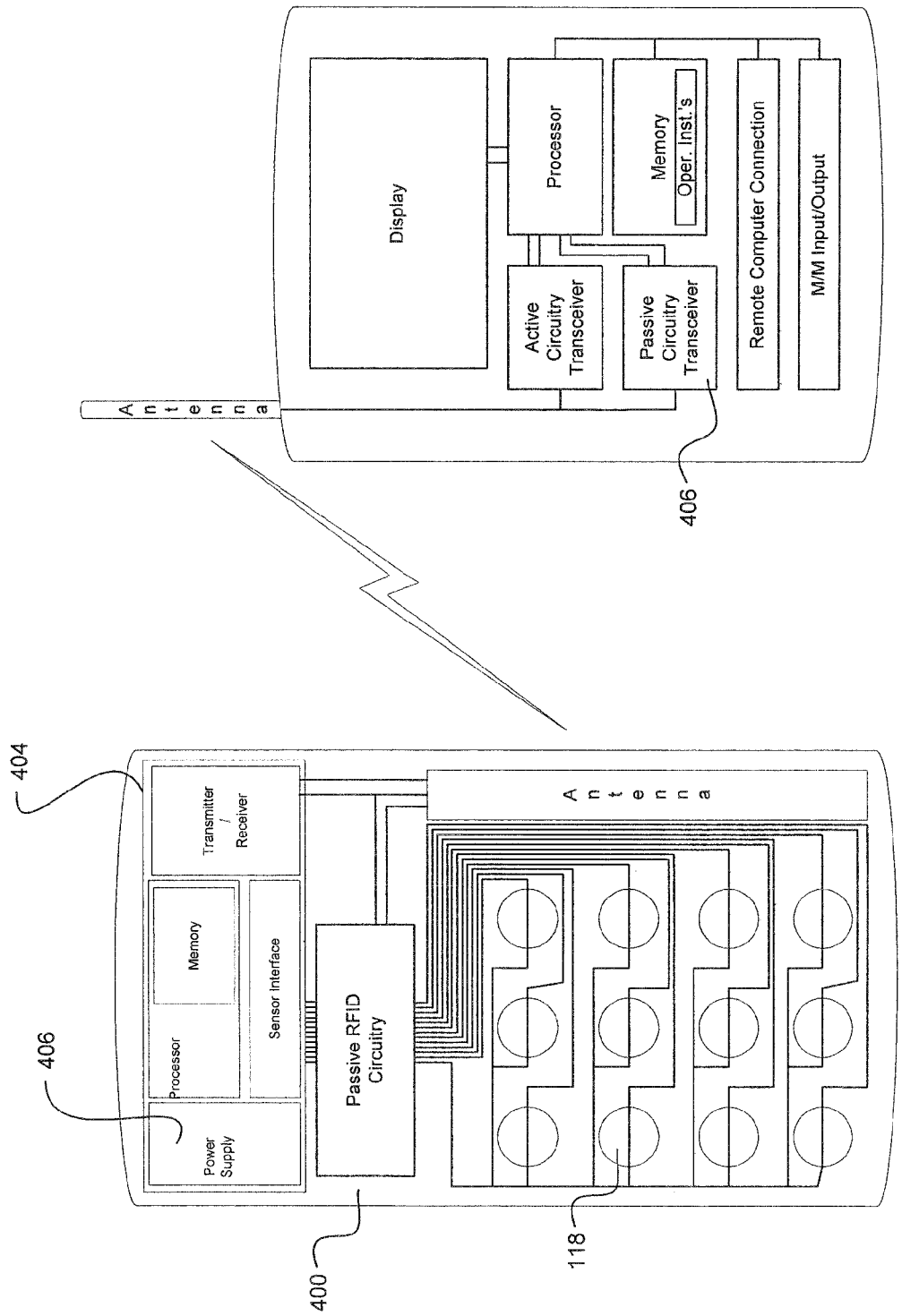
FIG. 4 shows a hybrid passive and active circuitry instrumented medication package associated with monitoring capabilities according to the present invention.

The limitation of active monitoring capabilities inherent in a passive RFID only equipped instrumented medication package may be overcome by implementation of hybrid passive and active circuitry on an instrumented medication package. FIG. 4 shows a hybrid instrumented medication package 400 utilizing both passive RFID circuitry 402 for monitoring the package before the package is dispensed, as well as active circuitry 404 for more specifically monitoring the accessing of medication after dispensation. The active circuitry 404 may be provided with a switch (not shown) for connecting a power source to the circuitry, such as described in applicant's U.S. patent application Ser. No. 10/234,021, titled "Power Control For Instrumented Medication Package" and filed herewith. The use of a switch to enable connecting the power source 406 at the time of dispensation allows the use of a smaller power supply 406, as the power supply 406 does not need to provide energy prior to the package being dispensed.

The passive circuitry 402 and active 404 circuitry may be embodied in separate passive REID and active RFID chips, with the active RFID chip being provided with sufficient capabilities to monitor times at which medication was accessed, times at which medication was due to be taken, expiration dates, or environmental sensors to monitor patient storage of the instrumented medication package.

Such a hybrid active and passive system would allow monitoring of the package while the package was in storage, such as in a pharmacy area, as well as monitoring of the package while the package was near a medication monitor. As discussed above, the medication monitor could be communicably connected to a network to allow dissemination of information received from the package to relevant parties, or communication of information from relevant parties to the package, such as to allow the downloading of medication times, or an expiration date. As is evident from this instruction, information such as medication times or expiration dates would not need to be downloaded to the package at the time of production, simplifying the task of providing requisite storage for the information on the instrumented medication package.

The circuitry necessary to provide severable conductors 118 for each containment, for both the active circuitry and passive circuitry, could be accomplished by utilizing the same circuitry for both aspects of the circuitry, or by providing redundant severable conductors 118. Redundant severable conductors 118 could be accomplished though the printing of multiple conductive layers onto the package closure.

The ability of the RFID chip to be hardwired allows the chip to function without first requiring the chip to determine its internal operating instructions. This capability may allow enhanced monitoring of the contents of an instrumented medication package 102 to which passive RFID circuitry 402 is attached when the passive RFID circuitry 402 is combined with an instrumented medication package 102. By integrating the severable conductors of an instrumented medication package 102 into the circuitry of the RFID chip, the circuitry of the severable conductors may be used to form a portion of the RFID circuitry, such that a portion of a response identifier generated by the passive RFID chip may be determined by the condition of the severable conductors. This may allow continuous monitoring of the severable conductors when the instrumented medication package 102 is within the transmission range of a requisite RE transmitter, without requiring an internal power source. Although the integration of the severable conductors 118 with passive REID circuitry 402 does not provide for monitoring of times at which severable conductors 118 are severed locally, it does allow an RF receiver associated with the RF transmitter, (together embodied in a passive circuitry transceiver 404) to monitor the responding identification information, such that the severing of a severable conductor 118 will change the identification code transmitted by the passive REID circuitry 402, allowing a central station (not shown) receiving information via the Passive Circuitry Transceiver 404 to detect the severing of a severable conductor 118 within an instrumented medication package incorporating passive RFID circuitry 404.

As theft of medications is an important issue in hospital pharmacies, the incorporation of such a system into a hospital pharmacy may allow accessing of medication within the range of a RF transmitter/receiver pair to be detected when medications are accessed within a pharmacy. Such a capability may be used to reduce the unauthorized access to controlled substances, such as pain killers, since the accessing of medication within a containment may be rapidly communicated to the RF transmitter/receiver pair. Thus, control of the medication contained within an instrumented medication package may be monitored when the instrumented medication package is within a hospital pharmacy, allowing improper accessing of controlled substances to be detected and responded to.

Figure 5:
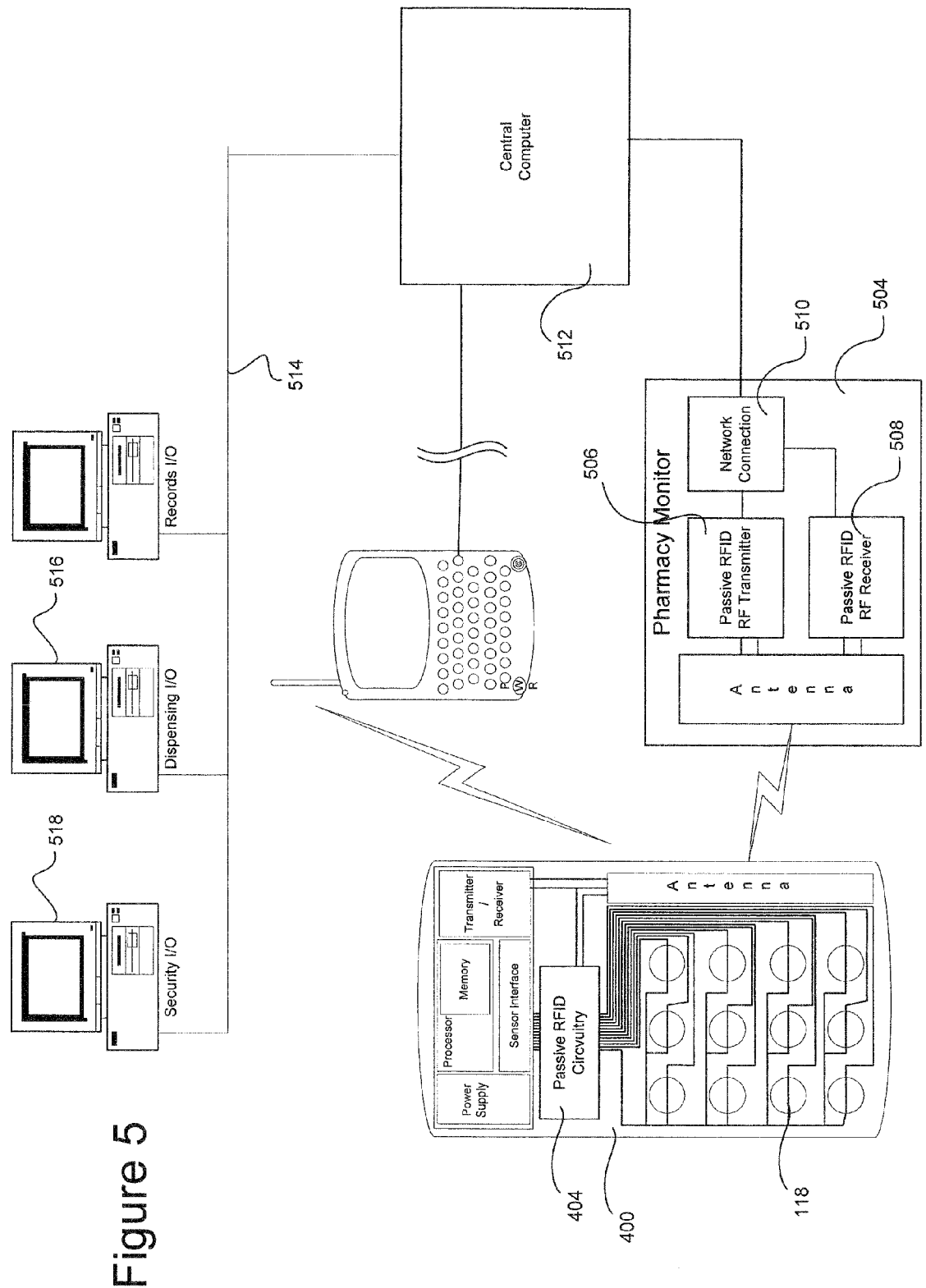
FIG. 5 shows a hybrid passive and active circuitry instrumented medication package implemented in a pharmacy environment.

A system embodying such a concept in a pharmacy environment is show in FIG. 5. The hybrid instrumented medication package 400 may be equipped with a passive RFID circuitry 404 connected to severable conductors 118, such that the severable conductors 118 form a portion of the passive RFID circuitry 404. The passive RFID circuitry may be installed on an instrumented medication package 502, such that the severable conductors 118 are multiplexed to reduce the number of necessary leads. Power received by the passive RFID circuitry may be applied to one end of each severable conductor 118, with the severable conductors 118 functioning as switches for generating an identification signal. For example, considering the identification to be a digitally encoded identification, where the passive RFID circuitry 404 receives power from a severable conductor lead (indicating continuity of the lead), the passive RFID circuitry 404 may transmit a 1, while where no power is received at the lead, the passive RFID circuitry 404 may transmit a 0. The passive RFID circuitry 404 may have a number assigned, such as for example a product code for tracking purposes. The passive RFID circuitry 404 would thus transmit the product code, with the connector status code appended to the product code. As an example, if a hybrid instrumented medication package 400 was assigned a product code of decimal 2897 (binary 101101010001), and had 12 containments, each with a severable conductor, if 101101010001000001100000 in response to a signal received from a monitoring station 504 comprised of an RF transmitters an RF receiver, and a network connection.

In addition to the product code and status code, a unique identifier for the specific hybrid instrumented medication package 400 may also be implemented. For example, the passive RFID circuitry 404 may contain a series of internal circuits that may be originally continuous, but which may be broken through the application of a voltage exceeding the capability of the circuit. As such, the circuits may be selectively broken prior to the passive RFID circuitry 404 being connected to an instrumented medication package 102, in order to set a package specific code. Alternately, Programmable Read Only Memory (PROM) may be incorporated to allow programming of an identification into the RFID circuitry. Either method allows mass-produced chips to be customized based on an identity value. For example, using the above binary coding, the package could be assigned a package specific code of 101000010000 (or 1288 in base 10 numbering), such that the RFID would respond with 101101010001 101000010000 000001100000. The signal need not be in binary form, but may rather use any of a number of other forms, such as frequency modulation to reduce the duration of a transmission needed to transmit an identifier.

Additional identification may be implemented as desired. For example, rather than incorporating a specific package identifier, the identifier may relate to a production batch, allowing identification of a production site, production date, or lot shipping information. Alternate or additional information may include the National Drug Code, expiration date, and/or a manufacturer tracking identifier.

Deconflicting signals from a concentration of hybrid instrumented medication packages, such as could occur where a number of instrumented medication packages were stored in a pharmacy area, may be accomplished through several methods.

Instituting a delay, such that an passive REID circuitry would respond only periodically, would reduce signal overlap, such that the timing characteristics of a signal could be used to distinguish the signal of one passive RFID circuitry from other transmitting passive RFID circuitries. Alternately, transmission frequencies could be varied to allow differentiation between transmitting passive RFID circuitries.

A pharmacy area, or any other area where such monitoring is desired, such as in a drug store or nursing station, may be provided with an RF transmitter/receiver pair which is connected to a network connection. The network connection may be communicably connected to a central computer which stores information concerning medications. The central computer 512 may additionally be communicably connected, such as through a network 514, to a dispensing input/output station 516 (hereafter "DI/O station"), to allow a pharmacist to communicate dispensation of a hybrid instrumented medication package 400 to the central computer 512. Although the DI/O station 516 is illustrated as a typical desktop computer, the DI/O station 516 may be implemented in any device which can be communicably connected to the central computer 512 to allow a pharmacist or other entity dispensing medication from the pharmacy area to communicate with the central computer 512. For example, a personal digital assistant, provided with the relevant operational capability, could be used. Such an embodiment could additionally include an RF transmitter/receiver pair to allow a specific instrumented medication package identifier to be transmitted directly from a package to the DI/O station 516. The central computer 512 may additionally be provided with a means for indicating unauthorized accessing of a medication to a responsible third party, such as a security input/output (hereafter "SI/O device" 518). The SI/O device 518 could simply be a printer which prints out administrative reports regarding the status of instrumented medication packages, or could be a computer assigned to a group responsible for monitoring the unauthorized accessing of medications, such as a security group.

Use of such an instrumented medication package in the pharmaceutical system described is shown in the process illustrated in FIG. 6. Once an instrumented medication package was placed into the pharmaceutical area, the RF transmitter would transmit sufficient energy to generate a response by the RFID chip. The transmitted response would be received by the RF receiver, and communicated to the network connection. The network connection would then forward the transmitted information to the central computer. The central computer could then verify the status of the instrumented medication package by parsing the identification information received. The product code and package code portions of the identifier could be used to update an inventory list for the pharmacy area at which the identifier was received. The received status code could be tested to determine whether the status of the individual connectors had changed in transit, such as if medication was improperly accessed in transit. If a status change were detected, the central computer could notify the appropriate authorities, such as via a SI/O device as described above. The status of the package would continue to be monitored while the instrumented medication package was stored in the pharmacy area. As such, should medication contained in the package be accessed improperly, the access would be detected, such that the improper accessing could be attributed to the person improperly accessing the package.

Tracking of the instrumented medication package could be discontinued once the instrumented medication package was transferred from the pharmacy area, or if the instrumented medication package was dispensed. Information regarding such transfer or dispensation could be provided to the central computer via the DI/O station, such that the central computer could account for dispensation into a patient's bill, or monitor transfer to ensure that a package reached a transfer destination. Should medication be accessed during transit, the accessing would be detected once the medication package reached its destination, such that the task of identifying who accessed the medication would be limited to those responsible for the transfer.

Combined Process

The present invention may be embodied in a process integrating an instrumented medication package within a health care system, as shown in FIG. 6. In order to provide for security tracking of a hybrid passive and active IMP (hereafter referred to as a "HIMP") stored within a pharmacy area, a passive monitor or monitors may be located 602 in the pharmacy area. The locating 602 of the passive monitor may allow passive circuitry indicating the presence of HIMP to be activated by the passive monitor, through the passive monitor transmitting 606 and trigger signal which causes a response 608 from the HIMP indicating the identity and containment status of the HIMP. The passive monitor is preferably communicably connected with a central computer, such that the central computer can coordinate information associated with the HIMP, as well as with involved physicians, patients, pharmacists, and/or other individuals or entities involved in the healthcare process.

A HIMP will typically be delivered 604 to a pharmacy area as part of a restocking evolution. The HIMP may be transported from a prior holding area, such as a pharmaceuticals storage area, or from the pharmaceuticals manufacturer. Data and information concerning the HIMP may typically be maintained by the entity storing the HIMP prior to delivery to the pharmacy, such that a record as to the status of containments within the HIMP may be made available to or transferred to the central computer. This data may form a baseline for status monitoring by the central computer.

As part of normal monitoring, the passive monitor may transmit 606 a trigger signal to which the HIMP is responsive, generating a response 608 from the passive circuitry contained on or in the HIMP. If the trigger signal is particular to a HIMP, the central computer may forward an instruction to the passive monitor to generate the trigger signal to detect the particular HIMP. For example, where a pharmaceutical manufacturer was shipping a quantity of medication contained in HIMPs to the pharmacy area, the pharmaceutical manufacturer could inform the central computer in advance of the pending shipment, as well as the specific trigger signal information associated with the HIMPs, as well as information concerning status of the containments within the HIMPs. Such information could be contained as part of routine invoicing documents generated in response to an order for medication.

In response to the trigger signal, the HIMP could transmit 606 with an identifier and containment status. Containment status may be of particular import where the medication contained in the HIMP is a controlled substance, such as a pain killer. This response would be received 610 by the passive monitor, informing the passive monitor of the presence and status of the HIMP.

If the passive monitor does not detect 610 a response from the HIMP, the central computer may be informed 612 of the lack of a response. A lack of a response may indicate that the HIMP has been removed from the pharmacy area, or is out of range of the passive monitor. Either way, the pharmacy may likely have an interest in investigating the lack of a response to ensure that the HIMP, and the medication contained therein, is not missing. Alternately, where the passive monitor is merely responsible for forwarding received responses, the determination that a response that should have been received was not may be made by the central computer. In such a case, the central computer would track the inventory of the pharmacy. When a HIMP is recorded as having been delivered to the pharmacy area, the central computer would monitor for responses forwarded from the passive monitor. If no responses were received, the central computer could institute actions as desired, such as notice to a pharmacist to verify the presence of the HIMP in the pharmacy area, or instructions to security to determine the location and status of the HIMP.

If the passive monitor detects 610 a response, the passive monitor may forward 614 the received response to the central computer. The form of the response may be determined by the manner chosen of distributing monitoring responsibilities. If all processing is to be accomplished by the central computer, the passive monitor may merely relay the response from the HIMP to the central computer. If the passive monitor is assigned processing tasks, such as testing the reported status of containments against a prior status to detect changes, the passive monitor may only report a "no change" report for a particular HIMP. Such distribution of tasking may be dependant upon the architecture chosen to implement the central computer, passive monitor, and the communications connection between them. Accordingly, the form of the response may even be a non-transmission, in the case of a protocol reporting only changes in status. The response of the central computer 616 is discussed further below.

The passive monitor may continue to monitor the HIMP until it is determined 618 that the package has been dispensed from the pharmacy. Once it has been determined that the package has been dispensed, the central computer may be informed 620 that the package has been dispensed. Such information may be determined through a pharmacist or other dispensing entity entering information into a computer or network device. Alternately, a separate monitor may be implemented at a portal through which medication is dispensed, such that the portal monitor may detect a response from passive circuitry passing within range of the portal monitor.

As is evident from the potential use of such a portal monitor, additional monitors can be used at access points for the medication storage areas, allowing a delivery monitor to detect HIMP's being delivered, as well as HIMP's being dispensed. The use of the severable conductors 118 as a portion of the circuitry responsible for generating an identification response may allow additional security, in that removal of the circuitry forming the monitoring and response circuitry, such as when such circuitry is implemented through a chip attachable to a medication package having the requisite severable conductors, would prevent the HIMP from responding correctly to a monitor in the storage area.

Figure 6A:
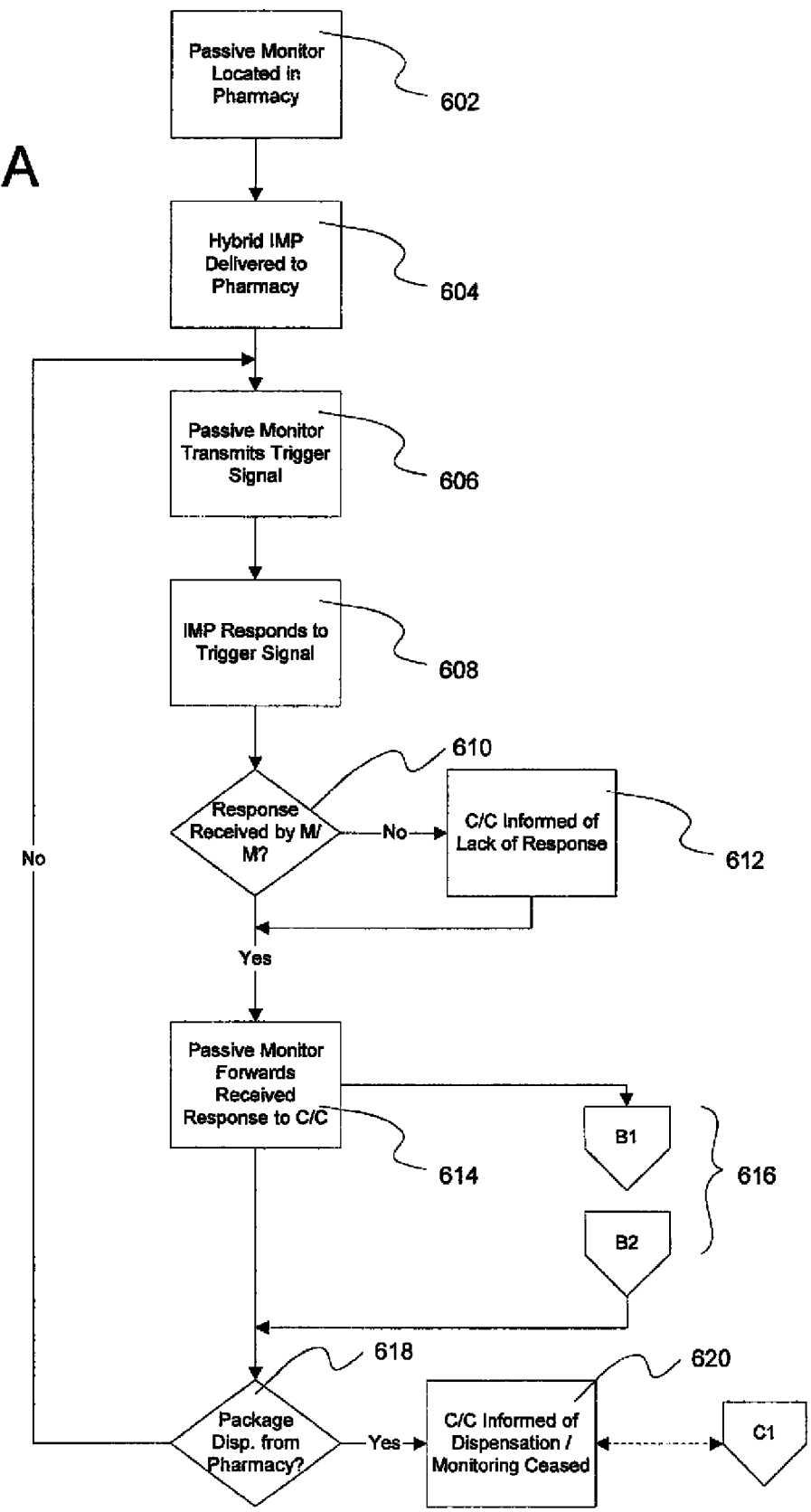
FIG. 6 shows a process flowchart illustrating a process of using a hybrid passive and active instrumented medication package according to the present invention.
Figure 6B:
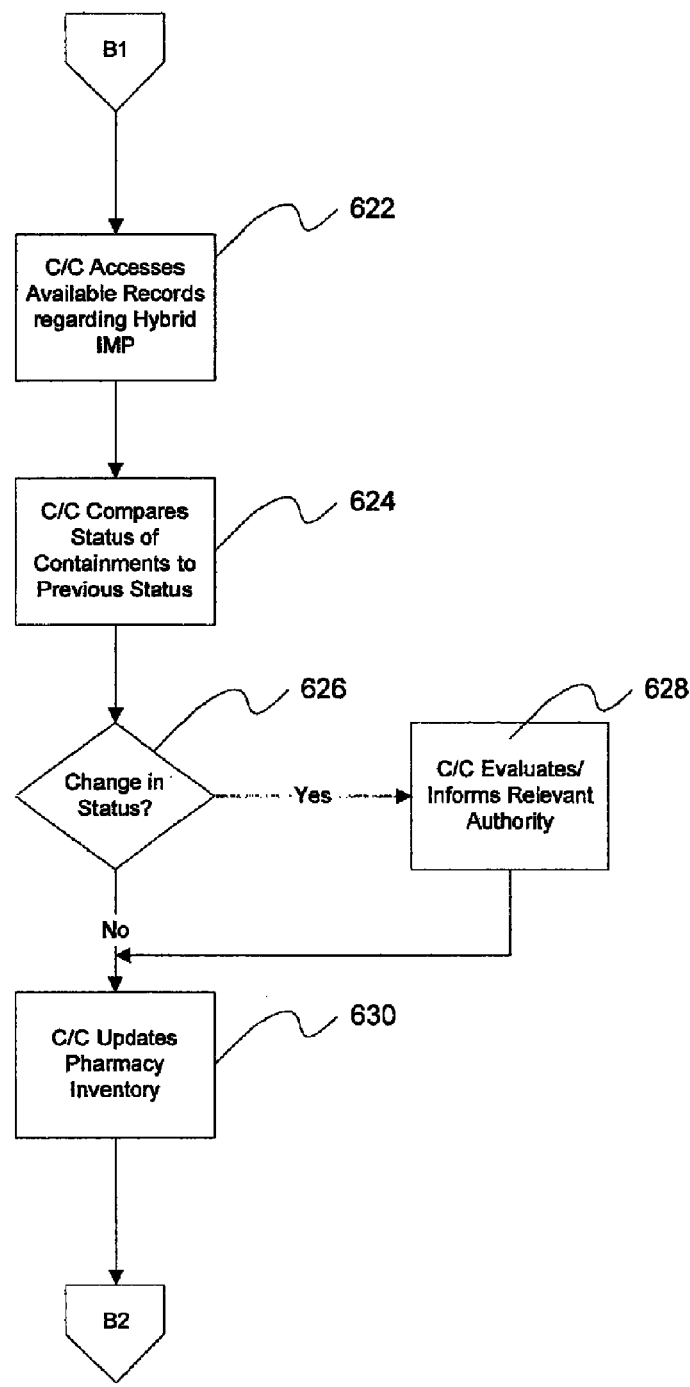

The process associated with the central computer monitoring a HIMP stored in a storage area is shown in FIG. 6B. When the central computer is informed 604 of the delivery of a HIMP, such as when the HIMP is delivered, the central computer may access 622 records, such as those previously stored, or such as provided by a pharmaceutical manufacturer or an entity responsible for transferring the medication, to receive a record regarding the condition of the HIMP. Initially, the central computer may presume the HIMP to be complete, such that the status of the severable conductors is initially assumed to be connected. For example, where 8 containments are included in the HIMP, and a 1 in the relevant position of the identification response indicates that a severable conductor has not been broken, the central computer can use 1111 1111 as the presumed identifier response, and base the generation of a notice upon the detection of a deviation from this code.

The central computer may compare 624 the status of the containments by comparing the status portion of the identifier code, such as by subtracting the previously stored code from the received code, and generating an alarm for any non-zero result. If a change in status is detected 626, the central computer may evaluate and generate 628 a notice to have the change in status evaluated by an entity responsible for the security of the HIMP. For example, a hospital administrator may be informed, allowing the hospital administrator to manually verify the condition of the HIMP. The simple notice function alone may assist in reducing unauthorized accessing of medication, since persons responsible for the unauthorized access would be aware of the ability of the hospital administration to detect the unauthorized access in such a timely fashion as to associate the unauthorized access with individuals in the area where the unauthorized access takes place through the timely detection of the unauthorized access. Upon completion of the evaluation of a received status identifier, the central computer may also update 630 a database storing information on the HIMP, such as to record the status at the recorded time to allow tracking of when an access or unauthorized access occurred.

Figure 6C:
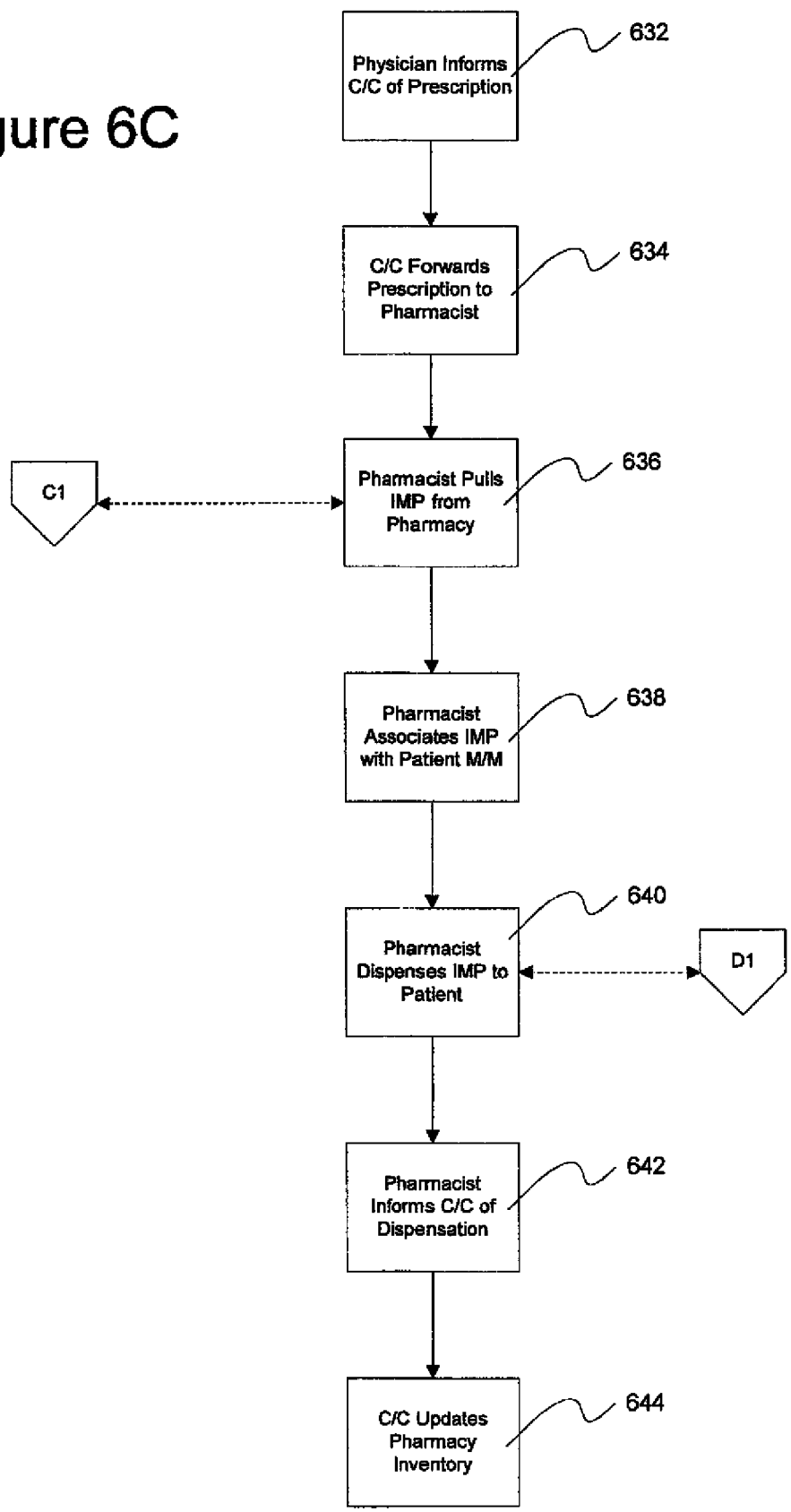

As shown in FIG. 6C, the administrative aspects of a physician prescribing medication may be integrated with the dispensing of an instrumented medication package to reduce the administrative tasking associated with prescribing the medication. This involvement may begin by the physician informing 632 the central computer of the prescription, potentially including dosing and scheduling information as may be typical of prescriptions. The central computer may then forward 634 the prescription information to a pharmacist, who can pull 636 the prescribed medication from the pharmacy storage area. The pharmacist may then associate 638 the specific instrumented medication package with the prescription prior to dispensing 640 the medication, such as by informing the central computer of the specific package number of the instrumented medication package being dispensed. The pharmacist may also enable active circuitry, such as by charging or recharging a power supply associated with the instrumented medication package, or by switching the package on if a switching capability is provided. Such a transition may also include disabling of the passive circuitry to prevent the passive circuitry from being read now that the package is associated with a particular package, and thus to some extent provides private patient information. As noted above, the pharmacist may inform 642 the central computer of the dispensation, such that a central database tracking medication information and patient records can be updated. Upon receipt of such notification, the central computer may also update 644 the inventory of the pharmacy, assisting in the replenishment of pharmacy stocks.

Figure 6D:
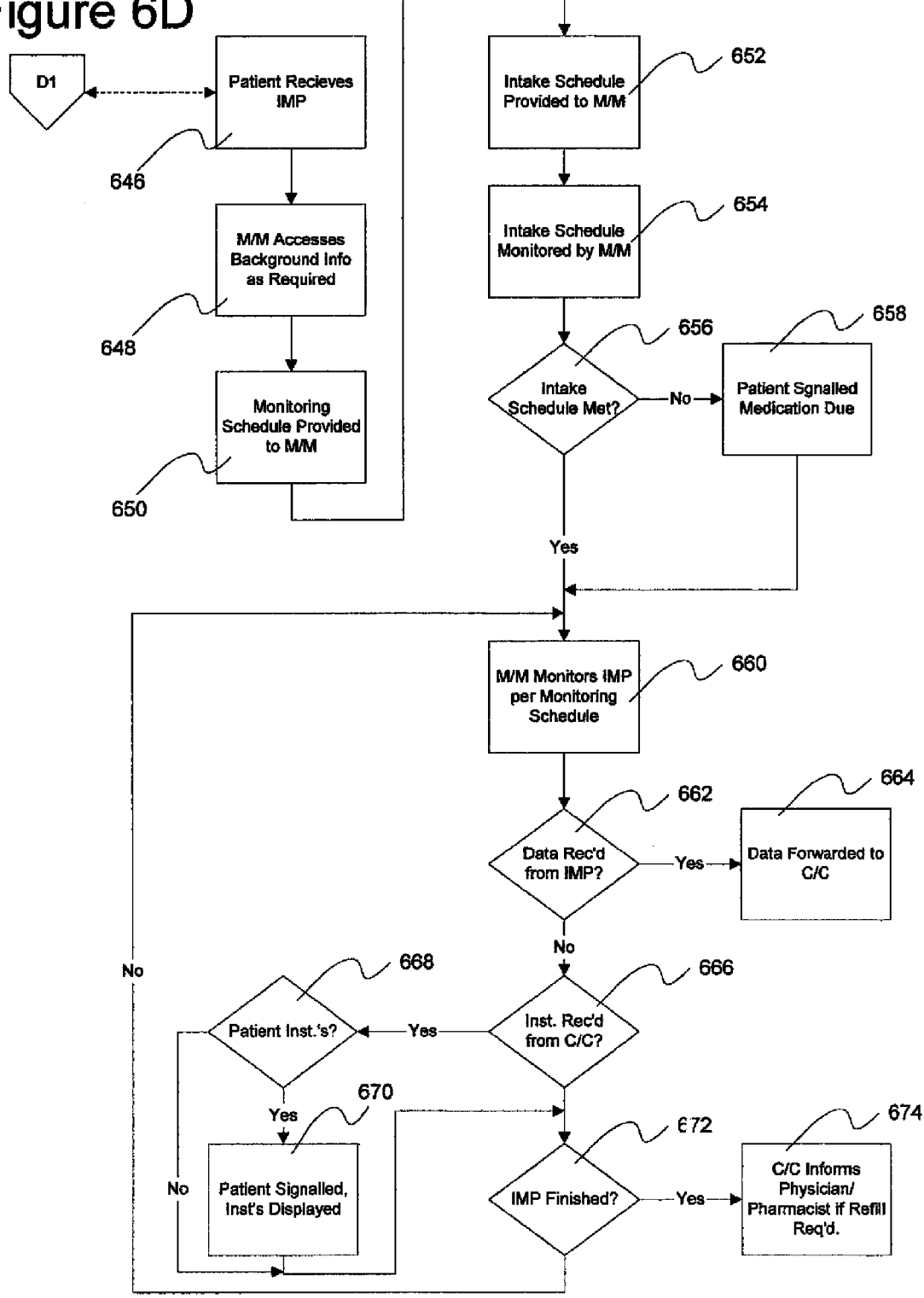

FIG. 6D shows a process according to the present invention involving an instrumented medication package associated with a patient to whom the package has been dispensed, illustrating the interaction between the patient and the data available from use of the instrumented medication package. Initially, the patient receives 646 the instrumented medication package. The patient may need to associate the instrumented medication package with a medication monitor, or the central computer may inform the medication monitor of the association with the instrumented medication package. The medication monitor may then access 648 background information associated with the particular instrumented medication package and medication contained therein. The background information may be instructions and warnings regarding the medication, notices regarding how the medication should be taken, or what activities should be curtailed while the medication is being taken. Such information may be displayed to the patient by the medication monitor, such as when a display or speaker is provided on the medication monitor. A monitoring schedule may be provided 650 to the medication monitor. The monitoring schedule may be dependant upon factors associated with the particular medication, such as the degree of adverse impact due to late taking of the medication by a patient, or the frequency with which the medication should be taken. The monitoring schedule may also be related to an intake schedule, such that the medication monitor would query the associated instrumented medication package to determine whether medication had been taken on time, based on the time when the medication was to be taken. The monitoring schedule does not need to be fixed or periodic, but may be varied as required. For example, where no access to medication is detected at a scheduled intake time, the periods between repeat queries may decrease the longer the time past the scheduled intake time.

An intake schedule 652 may be provided to the medication monitor to assist in providing information to a patient taking a medication, such as through providing alarms when a scheduled dosage has been missed, or through being able to acquire and display for a patient information regarding adverse consequences of not following an intake schedule. Such an adverse consequence display could, for illustration purposes, inform the patient that the effectiveness of a course of medication is reduced by 25% when the intake schedule is not met, or that the likelihood of the medical condition developing a resistance to the medication increases by 25% when the intake schedule is not met.

The intake schedule may then be monitored 654 to assist a patient in following the intake schedule. It may not be desired to tie the monitoring schedule to the intake schedule such that information request transmissions are made in accordance with the intake schedule. If a medication is amenable to misuse, such as by taking the medication too fast, a patient taking medication before a scheduled intake time would not be detected in a timely fashion by queries generated only at intake times. Accordingly, the intake schedule may be a factor in the monitoring schedule, but may not be controlled by the intake schedule.

If an intake time arrives without a patient accessing a requisite containment 656, the medication monitor may generate 658 a signal to the patient that medication is due to be taken. The signal can be an audible, tactile, or visual display indicating to the patient that a scheduled intake event has been missed. For example, a buzzer or vibrator associated with the medication monitor may be actuated, with the signal not ceasing until manual intervention by the patient. As a medication monitor may not be continuously in contact with a patient, a buzzer or bell provides a greater physical range over which a signal can be received by a patient, while the use of a buzzer allows a quiet mode, such as if a patient is in a business setting where a buzzer or bell would be offensive.

The medication monitor could continue to monitor 660 the instrumented medication package in accordance with the monitoring schedule If data were received from the instrumented medication package, the data could be forwarded 664 to the central computer. The central computer could make this information available to a physician responsible or the medical care of the patient, to a pharmaceutical manufacturer or regulatory authority collecting data on the patient's compliance with the intake schedule, or to other entities involved in the healthcare process.

Instructions could also be transmitted 662 from the central computer to the medication monitor. Such instructions could alter the intake schedule, the monitoring schedule, or provide information for a patient associated with the medication monitor. For example, a patient could telephone a physician regarding complications associated with the taking of a medication. The physician could adjust the intake schedule for the medication, by informing the central computer of the changed intake schedule. The changed intake schedule could be transmitted from the central computer to the medication monitor, which could then prompt a patient associated with the medication monitor in accordance with the changed intake schedule. Alternately, a physician could have information regarding a complication forwarded to the medication monitor for display to the patient. If the instructions received were patient instructions 668, the patient could be signaled 670, such as through an audible, tactile, or visual signal, and the instructions displayed for the patient on the medication monitor. The provision of the instructions through the medication monitor could also be used to document transmission to and receipt of the instructions by the patient, such as by having the instructions remaining displayed on the medication monitor until a patient indicates understanding of the instructions.

Finally, if the medication monitor had been provided with information regarding the total number of medication containments included in an instrumented medication package, the medication monitor could monitor the number of medication containments remaining unaccessed to determine whether the HIMP was finished 672, and inform 674 the central computer when the medication package had been completed, or inform the central computer in advance of completion of the medication in the medication package to allow a refill to be prepared.

As is evident from the above description, the present invention may be embodied in other specific forms than the embodiments described above without departing from the spirit or essential attributes of the invention. Accordingly, reference should be made to the appended claims, rather than the foregoing specification, as indicating the scope of the invention.

The invention claimed is:

1. A portable medication monitor, comprising:
  a housing containing a portable general purpose computer;
  a transmitter attached to said housing for transmitting a trigger signal to an instrumented medication package;
  a receiver attached to said housing for receiving a signal transmitted from the instrumented medication package in response to the trigger signal, said received signal including data identifying a status of each of a plurality of severable conductors associated with a respective plurality of medication containment cells; and
  software for monitoring said data received from said instrumented medication package associated with said portable medication monitor, the software configured to generate an alarm identifying that a scheduled dosage had not been taken based on the data received from the instrumented medication package in response to the trigger signal and a dosage schedule stored in a memory connected to the housing.

2. The portable medication monitor according to claim 1, wherein said transmitter is configured to wirelessly transmit the trigger signal.

3. The portable medication monitor according to claim 1, wherein said software comprises instructions which when executed attempt communication with a remote computer via a network connection in accordance with a predetermined schedule, said communication attempts being repeated until said communication is successful.

4. The portable medication monitor according to claim 1, wherein the trigger signal transmitted by said portable medication monitor is unique to the instrumented medication package.

5. The portable medication monitor according to claim 1, wherein the data transmitted in response to the trigger signal comprises time information associated with a patient's accessing of medication contained in the instrumented medication package associated with said portable medication monitor.

6. The portable medication monitor according to claim 1, wherein the signal transmitted by the instrumented medication package in response to the trigger signal includes data associated with a patient's accessing of medication contained in the instrumented medication package associated with said portable medication monitor.

7. The portable medication monitor according to claim 6, wherein the portable medication monitor is configured to transmit the data received from the instrumented medication package in response to the trigger signal to a remote computer.

8. The portable medication monitor according to claim 1, further comprising a display coupled to the housing, the display for displaying the dosage schedule and the status of the severable conductors of the instrumented medication package.

9. The portable medication monitor of claim 1, wherein the software is configured to generate one of a second trigger signal or an alarm if a response to the trigger signal is not received within a period of time.

10. A medication monitor, comprising:
  a housing containing a portable general purpose computer;
  a transmitter attached to the housing for transmitting trigger signals to a plurality of instrumented medication packages associated with the medication monitor, the trigger signals being unique to each of the plurality of instrumented medication packages;
  a receiver attached to said housing for receiving response signals from each of the plurality of instrumented medication packages, the response signals generated in response to receiving the trigger signals and including information relating to a removal of a dosage from at least one of a plurality of medication containment cells having a severable electrical connector attached;
  software for monitoring the information received from the instrumented medication packages in response to the trigger signals, the software configured to generate an alarm identifying that a scheduled dosage had not been taken based on the information received from one of the instrumented medication packages in response to a trigger signal and a dosage schedule stored in a memory connected to the housing; and
  a display coupled to the housing and configured to display the dosage schedule and a status of each of the severable conductors of the instrumented medication packages.

* * * * *